United States Patent [19]

Tzori

[11] Patent Number: Plant 6,295

[45] Date of Patent: Sep. 20, 1988

[54] EARLY TABLE GRAPE 'TZORI'

[76] Inventor: Moshe Tzori, D.N. Nahal-Lakhish Tsafon, Moshav Nir-Banim, 79433, Israel

[21] Appl. No.: 873,173

[22] Filed: Jun. 6, 1986

[51] Int. Cl.[4] ..... A01H 5/00

[52] U.S. Cl. ..... Plt./47

[58] Field of Search ..... Plt./47

[56] References Cited

U.S. PATENT DOCUMENTS

P.P. 4,329 10/1978 Kitahara ..... Plt. 47

P.P. 4,787 11/1981 Olmo et al. ..... Plt. 47

*Primary Examiner*—James R. Feyrer

*Attorney, Agent, or Firm*—Browdy and Neimark

[57] ABSTRACT

A very early seedless white table grape of which the individual berries are significantly larger than the parent, of which the grape of the invention is a mutant.

5 Drawing Sheets

This invention relates to a new and distinct variety of *Vitis vinifera*. The variety of the invention (denominated TZORI) is a very early seedless white table grape, of which the bunches are not overcrowded, the new grape being distinguished by the fact that both the bunches and the individual berries are significantly larger than the parent, from which the new grape is derived.

The new variety is further characterized by the facts that it is triploid, and very fertile and fast-growing. Characterization of the new variety as triploid was effected by means of a chromosome count carried out by the Volcani Institute, Bet-Dagan, Israel. Moreover, it reacts well to spraying with Giberellin hormone; at a concentration of 20 ppm, spraying at stages of 30% and 80% flowering, and after fruit set, with intervals of four days between sprayings, results in reducing the density of the bunch and enlarging the size of the berry.

The new grape was discovered as a mutation of the Perlette species, in 1978, in a vineyard at Nir-Banim, Israel. Propagation is by asexual reproduction from cuttings. Propagation has also been achieved by grafting the new variety onto the following stocks: 41.B, 161/49, Richter 110 and Saltcreek. The new variety has been tested for a period of two years by the Ministry of Agriculture, Plant Breeders' Rights Council, Bet Dagan, Israel. The grape of the invention is a table grape, intended for eating in a fresh state or for drying for eating as raisins.

DESCRIPTION OF THE FRUIT

The bunches are significantly less dense than the parent variety and are of medium size, but larger than in the parent. The peduncle has medium length, its lignification is weak. The individual berries have a round shape and are of circular cross-section; in formal terms they are of medium size, but are substantially larger than the berries of the parent variety. The skin is thin and green-yellow to yellow in color, that is to say the color is almost identical to Perlette although slightly more amber. The bloom on the skin is weak. The flesh is juicy, tender, and colorless. The berries are seedless. The pedicel is thick and of medium length. Separation of the berry from the pedicel is easy. The ripe berries have a slight Muscat-like flavor (the fruit of Perlette, by contrast, is tasteless); they contain a little more sugar and a little less acid than Perlette.

The new variety of the invention blossoms approximately 12 days earlier than Perlette and ripens early, also approximately 12 days earlier than Perlette. The produce may be harvested mid-June in Nir-Banim. It is desirable to harvest in two stages.

PLANT CHARACTERISTICS

Time of sprouting: Early.

Young vine-cane: The shoot tip is open, anthocyanin coloration is absent therefrom, hairs on the tip are either absent or very sparse.

Mature leaf: Of medium size, pentagonal shape, five-lobed and slightly thicker than in the case of Perlette. The upper side of the leaf blade is dark-green. The teeth are long, but the length to width ratio of the teeth is small. Both sides of the teeth are rectilinearly-shaped. Petiole sinus is very wide open, with a V-shaped base. In the main veins on both the upper and lower sides of the blade, the anthocyanin coloration is either non-existent or very weak. The density of either erect or prostrate hairs *between* the main veins on the lower side of the blade is sparse. There are no hairs *on* the veins on the upper side of the blade. The density of either erect or prostrate hairs *on* the main veins on the lower side of the blade is sparse. The petiole is shorter than the middle vein; the density of either erect or prostrate hairs on the petiole is sparse.

Figure 1:
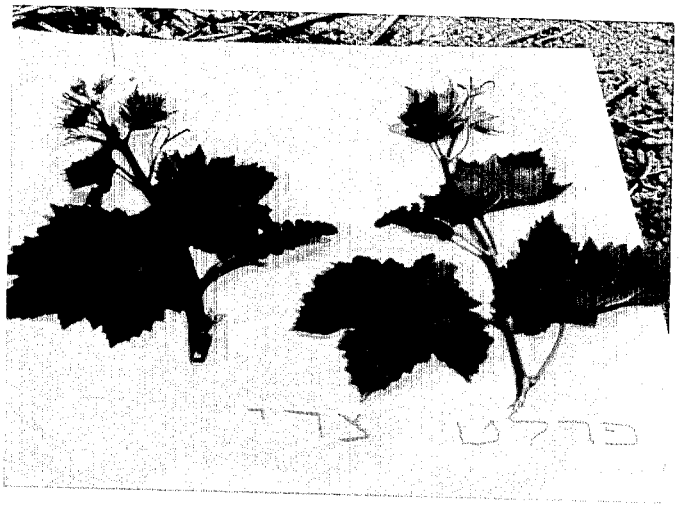
FIG. 1 compares the sizes of a typical shoot tip of the new variety, including an incipient grape cluster (left hand side) and the parent Perlette (right-hand side).
Figure 2:
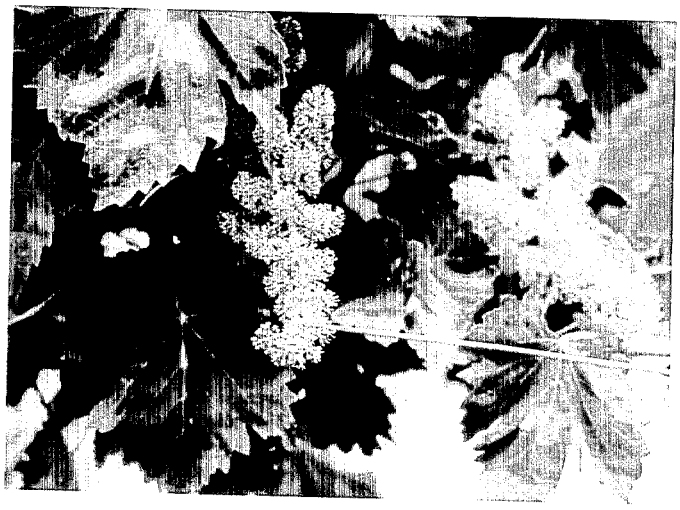
FIG. 2 illustrates grape clusters of the new variety in a blooming stage.
Figure 3:
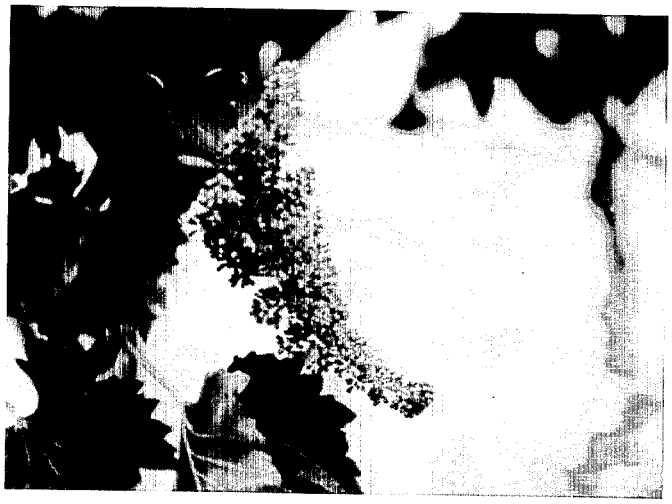
FIG. 3 is similar to FIG. 2, but at a slightly later stage.
Figure 4:
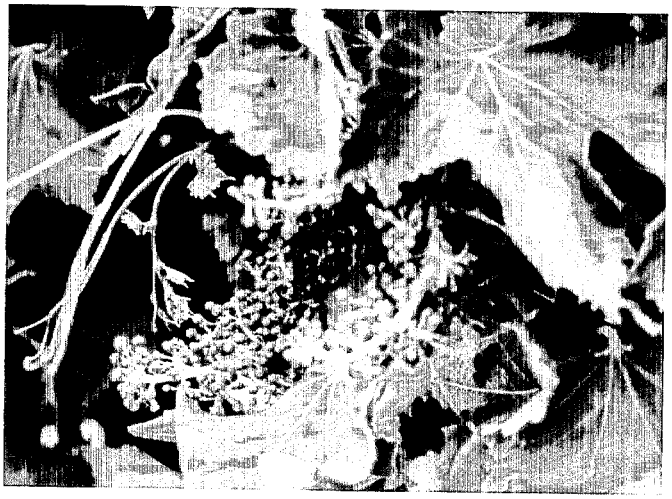
FIG. 4 shows a still later stage in which the formation of the individual berries has become more readily apparent.
Figure 5:
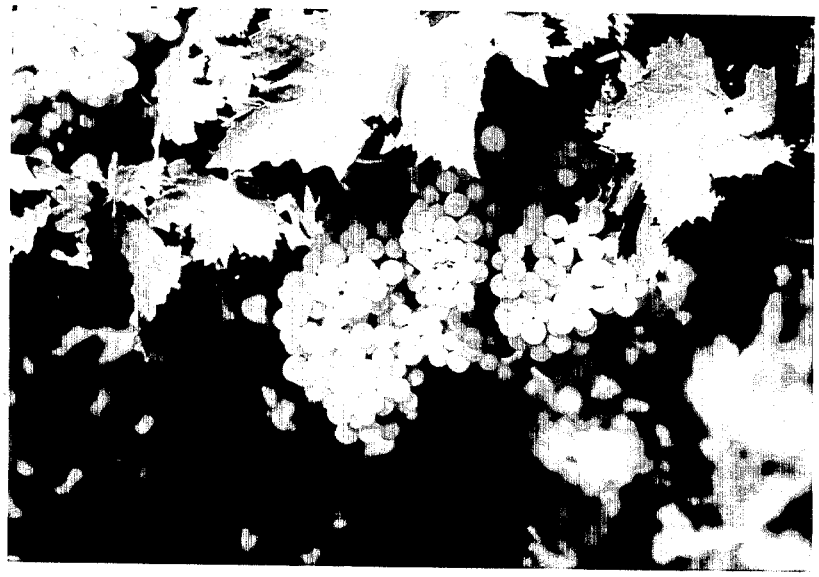
FIG. 5 shows bunches of grapes of the new variety, in situ.
Figure 6:
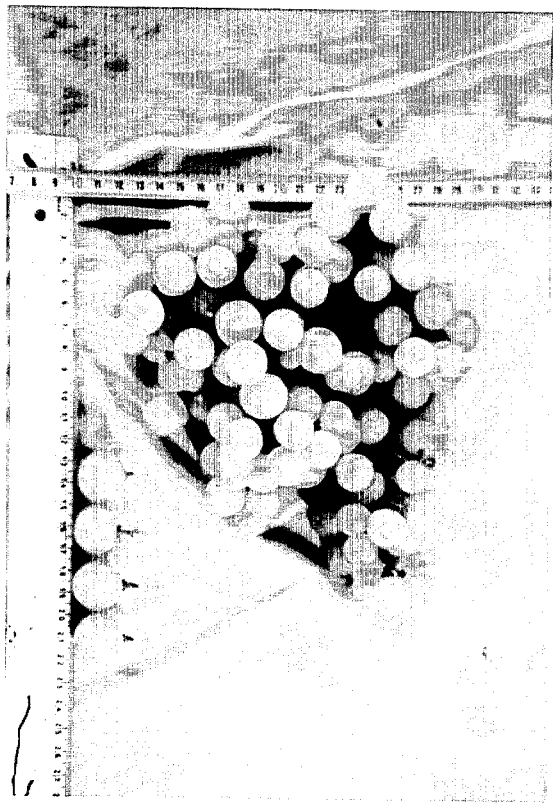
FIG. 6 illustrates the sizes of a bunch and of individual berries, of the new variety.
Figure 7:
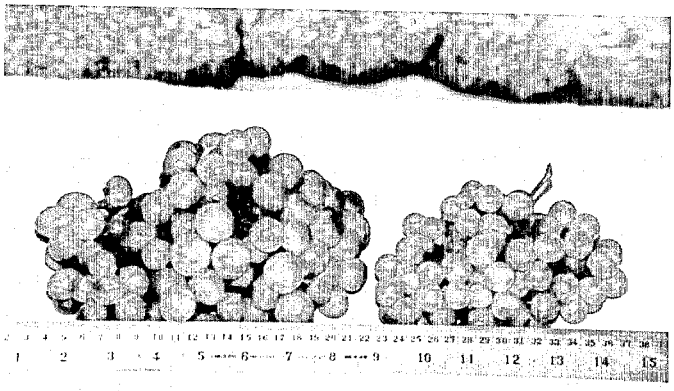
FIG. 7 compares the sizes of mature bunches of the new variety (left-hand side) and the parent Perlette (right-hand side), both the new variety and the parent having been subjected to the same treatment with Giberellin hormone, as has been described above.
Figure 8:
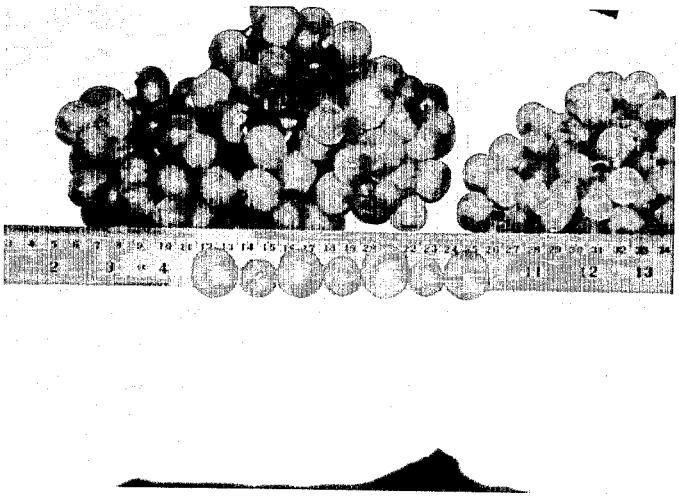
FIG. 8, foreground, compares the sizes of individual berries of the new variety, see the four large grapes, interspersed with three smaller grapes of the parent variety.
Figure 9:
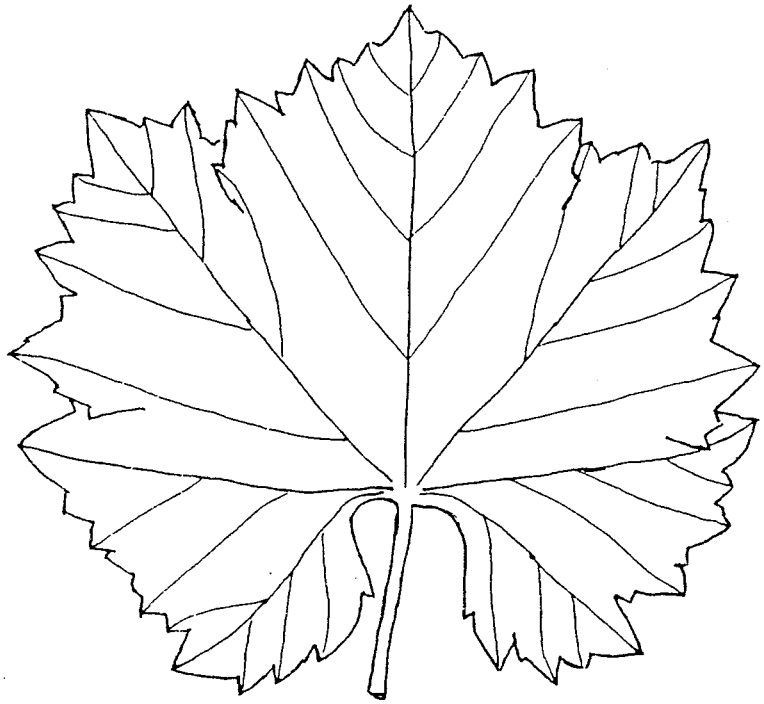
FIG. 9 is a drawing of a typical leaf of the new variety.

Flower: Perfectly formed. The overall coloring of the plant is similar to, but the stem is substantially thicker than, the parent Perlette. The latter characteristic can be seen in FIG. 1.

I claim:

1. The new and distinct variety of very early table grape substantially as described and illustrated herein. being distinguished by the fact that both the bunches and the individual berries are significantly larger than the parent, of which the new grape is a mutant.

* * * * *